(12) United States Patent
Borodic et al.

(10) Patent No.: US 8,192,979 B2
(45) Date of Patent: Jun. 5, 2012

(54) COMPOSITIONS, METHODS AND DEVICES FOR PREPARING LESS PAINFUL BOTULINUM TOXIN FORMULATIONS

(75) Inventors: Gary E. Borodic, Kensington, MA (US); Martin A. Acquadro, Wellesley, MA (US)

(73) Assignee: Botulinum Toxin Research Associates, Inc., Quincy, MA (US)

( * ) Notice: Subject to any disclaimer, the term of this patent is extended or adjusted under 35 U.S.C. 154(b) by 1459 days.

(21) Appl. No.: 11/046,721

(22) Filed: Feb. 1, 2005

(65) Prior Publication Data

US 2006/0147471 A1 Jul. 6, 2006

Related U.S. Application Data

(60) Provisional application No. 60/640,231, filed on Jan. 3, 2005.

(51) Int. Cl.
*C12M 1/00* (2006.01)
*A61K 39/02* (2006.01)
*A61K 39/08* (2006.01)

(52) U.S. Cl. ............... 435/283.1; 424/234.1; 424/236.1; 424/247.1

(58) Field of Classification Search ............... 424/184.1, 424/234.1, 236.1, 247.1; 530/300, 324
See application file for complete search history.

(56) References Cited

U.S. PATENT DOCUMENTS

| | | | |
|---|---|---|---|
| 4,031,892 A | 6/1977 | Hurschman | |
| 4,171,698 A | 10/1979 | Genese | |
| 4,424,057 A | 1/1984 | House | |
| 4,983,164 A | 1/1991 | Hook et al. | |
| 5,041,088 A * | 8/1991 | Ritson et al. ................... | 604/88 |
| 5,512,547 A | 4/1996 | Johnson et al. | |
| 5,576,468 A | 11/1996 | Lubowitz | |
| 5,696,077 A | 12/1997 | Johnson et al. | |
| RE35,986 E | 12/1998 | Ritson et al. | |
| 5,846,929 A | 12/1998 | Johnson et al. | |
| 6,312,706 B1 | 11/2001 | Lai et al. | |
| 6,474,369 B2 | 11/2002 | Castellano | |
| 6,506,399 B2 * | 1/2003 | Donovan ....................... | 424/423 |
| 7,211,261 B1 * | 5/2007 | Moyer et al. ............... | 424/236.1 |
| 2003/0138437 A1 | 7/2003 | Hunt | |
| 2004/0126396 A1 | 7/2004 | Aoki et al. | |

FOREIGN PATENT DOCUMENTS

| | | |
|---|---|---|
| WO | WO 97/35606 * | 11/1997 |
| WO | WO-00/15245 A2 | 3/2000 |
| WO | WO-00/15245 A3 | 3/2000 |
| WO | WO-01/58472 A2 | 8/2001 |
| WO | WO-01/58472 A3 | 8/2001 |
| WO | WO-2004/060384 A2 | 7/2004 |
| WO | WO-2004/060384 A3 | 7/2004 |
| WO | WO 2004/060284 A2 * | 9/2004 |

OTHER PUBLICATIONS

Schantz, Edward J. et al, "Standardized Assay for *Clostridium botulinum* Toxins," Journal of The AOAC, vol. 61, No. 1, 1978.
Goodnough et al., "Stabilization of Botulinum Toxin Type A During Lyophillzation", Applied and Environmental Microbiology, Oct. 1992, p. 3426-3428, XP-001024270.
International Search Report and The Written Opinion of the International Searching Authority mailed Nov. 15, 2005 in application PCT/US2005/002685.

* cited by examiner

*Primary Examiner* — Vanessa L. Ford
(74) *Attorney, Agent, or Firm* — Milbank, Tweed, Hadley & McCloy LLP

(57) ABSTRACT

Devices, methods and kits are disclosed for preparing and administering less-painful formulations of *Botulinum* toxin. The devices, methods and kits of the present invention are comprised of or use an acidic formulation of *Botulinum* toxin, or, in certain embodiments, a freeze- or flash-dried composition of *Botulinum* toxin, having a long shelf-life which is subsequently mixed with an acid-neutralizing solution and, optionally a sequestration agent prior to administration to a patient in need thereof. The pH-neutralized formulation of *Botulinum* toxin is pharmaceutically acceptable for administration to a patient and is significantly less painful than acidic formulations of *Botulinum* toxin or formulations of *Botulinum* toxin having unnecessary antigens.

21 Claims, No Drawings

COMPOSITIONS, METHODS AND DEVICES FOR PREPARING LESS PAINFUL BOTULINUM TOXIN FORMULATIONS

The present application claims priority under 35 U.S.C. §119(e) to co-pending U.S. Provisional Application Ser. No. 60/640,231 filed Jan. 3, 2005, the contents of which are hereby incorporated by reference in their entirety.

FIELD OF THE INVENTION

The present invention is directed, in certain embodiments, to devices comprising at least two chambers for separately storing an acidic solution of *Botulinum* toxin and an acid-neutralizing solution. The two solutions are maintained out of fluid contact with each other, until such time as a barrier, septum (or septa) or membrane separating the two chambers is broken, punctured, ruptured, permeabilized or rendered ineffective in preventing mixing of the solutions, to thereby facilitate or allow the solutions to mix. The resultant, pH-neutralized solution comprising *Botulinum* toxin may be administered to a patient in need thereof and is less painful than acidic or antigen-containing solutions of *Botulinum* toxin. The invention is also directed to methods of preparing a pharmaceutical formulation of *Botulinum* toxin, as well as to kits useful for preparing and administering the pharmaceutical formulations of *Botulinum* toxin disclosed herein.

BACKGROUND

All publications and patent applications cited herein are hereby incorporated by reference into the present specification in their entireties.

*Botulinum* toxin-based pharmaceuticals have become a major therapeutic agent for use in non-surgical cosmetic procedures. These agents are also used extensively to treat pain and conditions associated with facial movement and head and neck disorders involving excessive muscle tone, activity or bulk.

To be economically viable, pharmaceutical preparations of *Botulinum* toxin must be formulated so that they have a substantial shelf-life, usually at least 6-12 months. Techniques used to maintain the shelf life of *Botulinum* toxin formulations have included freeze- or flash-drying the neurotoxin (e.g. BOTOX™, *Botulinum* toxin type A complex) or formulating the *Botulinum* toxin preparation as a liquid with a low pH (e.g. MYOBLOC™, *Botulinum* type B complex).

Pure *Botulinum* toxin proteins and *Botulinum* toxin-complexed proteins (such as, for example, *Botulinum* toxin protein complexed with hemaglutinin or *Botulinum* toxin protein complexed with non-hemaglutinin non-neurotoxin) are very stable at low, acidic pH but become increasingly unstable at higher pH (greater than about pH 6.8). Unfortunately, injectable preparations of *Botulinum* toxin that are formulated having an acidic pH (pH less than 7.0) cause local pain when administered to patients because of the acidic nature of the formulations. For example, MYOBLOC™, a currently-available liquid "ready-to-use" formulation of *Botulinum* toxin, is substantially more painful than BOTOX™. This is because the pH of MYOBLOC™ is about 5.6, which is much lower than the pH of BOTOX™, which is formulated at about pH 7.4 upon reconstitution from a freeze- or flash-dried preparation.

Elan pharmaceuticals, the makers of MYOBLOC™, have conducted studies with liquid preparations of *Botulinum* toxin type B in which they found that a pH of about 5.5 was necessary to achieve acceptable shelf-life stability at room temperature. Higher pHs could not be used. In contrast, BOTOX™ achieves its stability at pH 7.4 based on freeze- or flash-drying processes. The major drawback in using freeze- or flash-drying to stabilize BOTOX™ is protein denaturation which may lead to increased antigenicity. Increased antigenicity is a well-known problem associated with the production of pharmaceutical proteins that have been formulated using freeze- or flash-drying procedures. The reactions produced by increased antigenicity decrease efficacy and ultimately lead to resistance to the neurotoxin.

BOTOX™ is further hampered by the presence of sodium chloride within the pre-lyophilization fluid. The presence of salt results in additional protein denaturation due to hypertonicity which develops during the vacuum evaporation process employed in freeze- and flash-drying procedures. Furthermore, freeze- or flash-dried compositions of *Botulinum* toxin that began as solutions comprising a physiological saline mixture (such as is used with BOTOX™) have substantially less activity after freeze- or flash-drying than comparably prepared *Botulinum* toxin compositions using salt-free aqueous solutions.

To date, the effect of altering storage pH on regional denervation activity and LD50 Unit potency of injectable *Botulinum* toxin formulations has not been established. Although altering the pH certainly is helpful in enhancing shelf-life and stability, protein tertiary structure alteration caused by changes in pH may affect neurotoxin binding, tissue permeation and cell internalization rates.

Thus, the present invention is based on the observation that, because neither of the two *Botulinum* toxin formulations described above is optimal, *Botulinum* toxin formulations can be improved by 1) minimizing the amount of denatured protein (unnecessary antigen) in the final preparation; 2) maintaining a pH close to about 7.0 to about 7.4 in the final injection solution; and 3) increasing physician convenience.

Accordingly, the invention described herein is directed, in certain embodiments, to a novel way of storing and formulating pharmaceutically acceptable *Botulinum* toxin compositions so that they retain a long shelf-life, but can be administered in a form that is significantly less painful than other currently available preparations of *Botulinum* toxin. The inventors have found that by employing a dilution procedure immediately prior to administration to alter the *Botulinum* toxin formulation pH from acidic to approximately neutral or alkaline (pH=about 6.5 to about 7.4, or about 7.0 to about 7.5, preferably about 7.0 to about 7.4) a significantly less painful pharmaceutical preparation of *Botulinum* toxin may be made that does not sacrifice the stability or shelf-life of the preparation. The effective final potency of the preparation may be established using regional denervating assays comparing the acidic storage form of the formulation to the final diluted injectable formulation of the drug. Because the units of toxin contained in the pre-dilution liquid are labeled and known, a nomogram is available in the package insert of the preparation indicating the effect of a pH change and dilution change on the pre-injection (storage) form of the formulation.

SUMMARY OF THE INVENTION

The present invention is directed, in certain embodiments, to devices for preparing pharmaceutically acceptable compositions of *Botulinum* toxin, wherein the devices comprise at least two chambers, wherein a first chamber comprises an acidic solution of *Botulinum* toxin, and a second chamber comprises an acid-neutralizing solution. In certain embodiments, the devices of the invention may comprise at least three chambers. In still further embodiments, a third chamber comprises a solution comprising one or more sequestering agents.

In certain preferred embodiments of the invention, any of the devices described herein comprise one or more barriers or seals or septa separating the chambers. In preferred embodiments, the barriers or seals or septa may be broken or breached or ruptured or punctured or permeabilized or perforated to allow the contents of each chamber to mix. In still further embodiments of the invention, the devices described herein comprise one or more barriers, septa or seals which may be rendered ineffective in preventing mixing of the solutions and compositions described herein.

In certain embodiments of the invention, the devices described herein comprise one or more barriers or seals or septa, wherein said barriers or seals or septa comprise a membrane.

In further preferred embodiments of the invention, the acidic solutions of *Botulinum* toxin described herein have a pH of about 1.0 to about 6.9. Preferably, the pH of the acidic solutions of *Botulinum* toxin is about 2.0 to about 6.9. More preferably, the pH of said acidic solutions of *Botulinum* toxin is about 2.5 to about 6.8. Even more preferably, the pH of said acidic solutions of *Botulinum* toxin is about 2.5 to about 6.7.

In preferred embodiments of the invention, the acidic solutions of *Botulinum* toxin described herein and the *Botulinum* toxin compositions described herein may comprise any combination of one or all of immunotypes A-G. In still further embodiments of the invention, the acidic solutions of *Botulinum* toxin described herein and the *Botulinum* toxin compositions described herein comprise about 1 to about 2000 LD 50 units of *Botulinum* toxin.

In certain preferred embodiments of the invention, the acid-neutralizing solutions described herein comprise one or more weak bases. In further embodiments of the invention, said one or more weak bases comprise an inorganic base. In still further embodiments of the invention, said one or more weak bases comprise an organic base.

In certain preferred embodiments of the invention, the acid-neutralizing solutions described herein comprise one or more strong bases. In further preferred embodiments of the invention, said one or more strong bases comprise an organic base. In still further embodiments of the invention, said one or more strong bases comprise an inorganic base.

In certain embodiments of the invention, the acid-neutralizing solutions described herein comprise a buffering agent. In further preferred embodiments, the buffering agent is an organic buffer or an inorganic buffer or any combination of organic and inorganic buffers.

In certain embodiments of the invention, the acid-neutralizing solution described herein is present in an amount sufficient to raise the pH of the acidic *Botulinum* toxin solution to about 7.0 to about 7.5 after mixing. In further embodiments of the invention, the acid-neutralizing solution is present in an amount sufficient to raise the pH of the acidic *Botulinum* toxin solution to about 6.5 to about 7.45 after mixing. In still further embodiments of the invention, the acid-neutralizing solution is present in an amount sufficient to raise the pH of the *Botulinum* toxin solution to about 7.0 to about 7.4 after mixing.

In preferred embodiments of the invention, the acid-neutralizing solution is selected from the group consisting of a bicarbonate solution, a phosphate solution, a carbonate solution, a sodium hydroxide solution, a potassium hydroxide solution, a calcium hydroxide solution, an aluminum hydroxide solution, and any combination of these solutions.

In further embodiments, the invention is directed to devices comprising at least two chambers or optionally, at least three chambers, wherein a first chamber comprises a *Botulinum* toxin composition, and a second chamber comprises an acid-neutralizing solution, optionally, a third chamber may comprise a solution comprising one or more sequestering agents.

In certain embodiments, the *Botulinum* toxin composition comprises a lyophilized composition. In still further embodiments, the *Botulinum* toxin composition comprises a freeze-dried or flash-dried composition. In still further embodiments, the *Botulinum* toxin composition is salt-free. In other embodiments, the *Botulinum* toxin composition comprises one or more salts. In further embodiments, the one or more salts are selected from the group consisting of sodium chloride, potassium chloride, calcium chloride, ammonium chloride and any combination of these salts.

In certain embodiments, the acid-neutralizing solution is present in an amount sufficient to result in a pH of about 7.0 to about 7.5 after mixing with said *Botulinum* toxin composition. In further embodiments, the acid-neutralizing solution is present in an amount sufficient to result in a pH of about 6.5 to about 7.45 after mixing with said *Botulinum* toxin composition. In still further embodiments, the acid-neutralizing solution is present in an amount sufficient to result in a pH of about 7.0 to about 7.4 after mixing with said *Botulinum* composition.

The invention is also directed to methods of preparing pharmaceutical formulations of *Botulinum* toxin comprising combining an acidic solution of *Botulinum* toxin and an acid-neutralizing solution. In further embodiments of the invention, the acidic solution of *Botulinum* toxin and the acid-neutralizing solution are combined within any of the devices described herein.

The invention is also directed to methods of preparing a pharmaceutical formulation of *Botulinum* toxin comprising combining a *Botulinum* toxin composition and an acid-neutralizing solution. In further embodiments of the invention, the *Botulinum* toxin composition and the acid-neutralizing solution are combined within any of the devices described herein.

In further embodiments of the methods described herein, the pharmaceutical preparation of *Botulinum* toxin is prepared by mixing a measured volume of an acid-neutralizing solution with an acidic formulation of *Botulinum* toxin or a *Botulinum* toxin composition.

In still further embodiments of the methods described herein, the pharmaceutical preparations of *Botulinum* toxin are prepared by withdrawing a measured volume of an acid-neutralizing solution from any of the devices described herein and mixing said measured volume with an acidic *Botulinum* toxin formulation in any of the devices described herein.

In further embodiments of the methods described herein, the pharmaceutical preparations of *Botulinum* toxin are prepared by withdrawing a measured volume of an acid-neutralizing solution from any of the devices described herein and mixing said measured volume with a *Botulinum* toxin composition in any of the devices described herein.

In a still further embodiment of the methods described herein, the pharmaceutical preparations of *Botulinum* toxin are prepared by combining an acidic formulation of *Botulinum* toxin with an acid-neutralizing solution.

The present invention is also directed to kits comprising a device for preparing a pharmaceutical formulation of *Botulinum* toxin, wherein said kit comprises any of the devices described herein.

In a further embodiment of the present invention, the kits may comprise any of the acidic formulations of *Botulinum* toxin described herein and any of the acid-neutralizing solutions described herein.

In a still further embodiment of the present invention, the kits may comprise any of the *Botulinum* toxin compositions described herein and any of the acid-neutralizing solutions described herein.

In certain embodiments of the invention, the kits further comprises any of the sequestering agents described herein.

In certain embodiments, the kits may comprise an anesthetic. In preferred embodiments, the anesthetic is a local anesthetic. In further embodiments, the anesthetic is applied topically. In still further embodiments, the anesthetic is selected from the group consisting of lidocaine, marcaine, cocaine, and xylocaine. In certain preferred embodiments, the anesthetic is dissolved in any of the acid-neutralizing solutions described herein. In further preferred embodiments, any of the acid-neutralizing solutions described herein comprises an anesthetic.

DETAILED DESCRIPTION

The present invention is directed, in certain embodiments, to devices useful for storing solutions or compositions of *Botulinum* toxin having a long shelf-life. Immediately prior to administration to a subject, the devices may also be used to prepare less painful pharmaceutically acceptable formulations of *Botulinum* toxin for administration to a patient in need thereof.

The devices described herein are comprised of chambers separately containing an acidic solution of *Botulinum* toxin, an acid-neutralizing solution and, optionally a solution of a sequestration agent.

In one embodiment of the invention, the less painful *Botulinum* toxin formulations disclosed herein are made by a two-step method wherein an acidic liquid preparation of *Botulinum* toxin (which serves as the preservative vehicle for the active agent) is mixed with an acid-neutralizing solution. The pH of the acidic liquid solution is between about pH 1.0 to about pH 6.8, preferably, between about pH 2.5 to about pH 6.8. Attached but not communicating with the preservation vehicle is a second solution containing physiologic saline in solution with a sufficient amount of sodium bicarbonate (or phosphate or a suitable buffer), which, when combined with the preservation vehicle, increases the pH of the preservation fluid to about pH 6.5 to about pH 7.4, preferably, about pH 6.8 to about pH 7.4.

In certain embodiments, the physician or surgeon, just prior to utilizing the drug, breaks a seal separating the acidic preservation fluid from the acid-neutralizing solution to create a solution mixture at a pH of about 6.5 to about pH 7.5, or about pH 7.0 to about pH 7.5, preferably about pH 7.0 to about pH 7.4 which is significantly less painful than acidic solutions of *Botulinum* toxin. The lower pH preservation fluid necessary for shelf-life stability now becomes ideal for injection without causing discomfort or pain because the pH has been adjusted to about pH 6.5 to about pH 7.5 or about pH 7.0 to about pH 7.5, preferably about pH 7.0 to about pH 7.4.

Different embodiments of this invention may include dispensing the preservation (low pH) *Botulinum*-containing fluid with a container holding the second bicarbonate solution, which needs to be mixed prior to use. In one embodiment, a double chamber syringe may be used containing two or more chambers which are conjoined allowing solution mixture just prior to injection. In addition to bicarbonate, other bases may be used to neutralize the acidic *Botulinum* toxin preservation fluid.

A. Definitions

As used herein the term "buffering agent" means an aqueous solution that resists a change in pH upon addition of acid or base.

As used herein, the term "acid-neutralizing solution" means an alkaline solution that may be used to increase the pH of a solution above about pH 6.5.

As used herein, one LD50 unit of a *Botulinum* toxin is the dose necessary to kill 50% of a population of about 20 gram to about 30 gram Swiss-Webster mice.

As used herein, the term "nomogram" means a graphic representation that consists of several lines marked off to scale and arranged in such a way that by using a straightedge to connect known values on two lines an unknown value can be read at the point of intersection with another line.

As used herein, a "sequestration agent" or a "sequestering agent" means an agent that enhances localization and/or retention of *Botulinum* toxin to the site of administration.

As used herein, "effective amount" is an amount sufficient to produce a therapeutic response. An effective amount may be determined with dose escalation studies in open-labeled clinical trials or bin studies with blinded trials.

As used herein, a "subject in need thereof" is any patient having a condition that may be treated using a *Botulinum* toxin.

As used herein "salt-free" means a composition or a solution that contains less than about 2.0% salt by weight (w/w); or less than about 1.0% salt by weight (w/w); or less than about 0.5% salt by weight (w/w); preferably, less than about 0.25% salt by weight (w/w); more preferably, less than about 0.15% salt by weight (w/w); most preferably, less than about 0.05% salt by weight (w/w).

As used herein, an "acidic solution" is a solution having a pH less than about pH 7.0.

As used herein, the term "device" means a piece of equipment specially designed for the storage of formulations in a manner such that the formulations may be combined when desired within the device or outside of the device prior to administration to a subject in need thereof to yield a pharmaceutically acceptable formulation. The devices of the present invention may comprise an ampule, a cartridge, a vial, a syringe, a bottle, a jar, a graduated ampule, a graduated cartridge, a graduated vial, a graduated syringe, a graduated bottle, a graduated jar or any combination of the foregoing.

As used herein, a "pH-neutralized solution" means a solution having a pH of about 6.5 to about 7.5. Preferably, a "pH-neutralized solution" means a solution having a pH of about 7.0 to about 7.5. Most preferably, a "pH-neutralized solution" means a solution having a pH of about 7.0 to about 7.4.

B. Multi-Chamber Devices for Use with Syringes or Needle-Less Systems

Multi-chamber devices having at least two distinct chambers for use with syringes or needle-less injection systems are known. Such devices may be used for mixing a solid or liquid medicament with a liquid diluent prior to administration to a subject. The devices may comprise ampules, vials, cartridges, bottles or other such vessels that comprise two or more separate chambers. A *Botulinum* toxin formulation, as described further herein, is stored in one of the chambers prior to use in either solid or liquid form. A second chamber contains an acid-neutralizing solution as described further herein. Optionally, additional chambers may comprise one or more sequestration agents and/or additional excipients. Each of the chambers is separated from the other chambers by an impermeable membrane or barrier or seal or septum or rubber septum which may be permeabilized, or punctured, or ruptured or broken, such that the contents of each chamber is allowed to mix with the contents of the other chambers prior to administration to a patient.

It is contemplated that, in certain embodiments of the invention, the acidic *Botulinum* toxin formulation may be removed from a storage device and mixed with an acid-neutralizing solution in a separate device such as, for example, a syringe, vial, cartridge, bottle or ampule prior to administration to a patient in need thereof.

In further embodiments of the invention, the acidic *Botulinum* toxin formulation may be removed from a storage device and mixed with an acid-neutralizing solution and a sequestering agent in a separate device such as, for example, a syringe, vial, cartridge, bottle or ampule prior to administration to a patient in need thereof.

U.S. Pat. No. 4,171,698 describes a pre-filled, ready-to-use, disposable syringe wherein a fluid medicament and a diluent therefor are sealed in two separate telescoping syringe barrels. In another embodiment, a medicinal powder is sealed in an outer barrel adjacent to the nozzle section by means of a pierceable stopper and the diluent is sealed in an inner barrel between another pierceable stopper and a plunger stopper. A double-pointed cannula is positioned between the two pierceable stoppers by means of a telescoping guide arrangement. Movement of the plunger stopper inwardly in the inner barrel initially effects a piercing of both pierceable stoppers and intermixing of the medicinal powder with the diluent. Continued movement of the plunger stopper will expel the mixed medicament from the syringe.

U.S. Pat. No. 4,031,892 describes two-chamber syringes for mixing a powdered medicament with a diluent and then injecting the mixed ingredients into a patient. The syringe may include a vial formed with a single glass cylinder closed at one end by a plunger and at its other end by a pierceable diaphragm. An intermediate pierceable diaphragm divides the cylinder into upper and lower chambers, and is locked against axial movement relative to the cylinder. A powdered medicament is provided in the upper chamber and a diluent is provided in the lower chamber. The ingredients are mixed by inserting the vial into a cup-shaped holder having a hollow, pointed needle extending from the base of the holder. Axial pressure on the vial causes the pointed end of the needle to sequentially pierce the end and intermediate diaphragms, and to cause the diluent to flow into an opening in the sidewall of the needle, through the needle, and then into the upper chamber from the pointed needle end. The thus-mixed ingredients are dispensed by applying axial pressure to the plunger, or by drawing metered amounts into the medicament pressurizing chamber of a needle-less, hypojet injector.

U.S. Pat. No. 4,424,057 describes a wet-dry syringe for combining and mixing a liquid and a solid medicament or at least two dissimilar liquid medicaments prior to the application thereof to a patient includes a first vial having liquid or solid medicament disposed between a pair of identical vial seals. A second vial functions as a piston rod and includes a pair of end seals with a liquid medicament disposed therein. One of the second vial seals includes a hollow piercing needle which when utilized to pierce one end seal of the first vial causes the medicament therein to flow into the first vial thereby mixing the medicaments prior to application to a patient by means of a needle piercing assembly which pierces the second of the first vial seals and the patient to which the mixed medicaments are to be infused. The second vial functions as a piston rod and aides in the discharge of the medicaments.

U.S. Pat. No. 4,983,164 relates to an automatic two-chamber injector for mixing and injecting a medical solution. The injector comprises a barrel having a first end with a receiving portion for an injection needle, said portion being sealed prior to use, and a second end with a displaceable plunger. The barrel comprises two chambers separated by a migration-proof membrane, said membrane being adapted to rupture when the plunger is displaced towards the first end of the barrel. Also disclosed is a method for mixing and injecting a solution by means of an automatic two-chamber injector and to a cartridge for a two-chamber injector.

U.S. Pat. No. 5,041,088 is directed to a multiple chamber automatic injector having at least two chambers containing different ingredients of a medicament separated by an impermeable membrane. A lance is movable independently of a plunger to cut or pierce the membrane before a spring-loaded drive member for the plunger is released to drive a needle out of the body of the injector and discharge the medicament through the needle. A removable safety clip is provided for preventing movement of an actuating cap into an operative position for advancing the lance, and release of the drive member is preventable by a removable safety pin until the injector is to be used.

RE 35,986 is directed to a multiple-chamber automatic injector. An automatic injector is disclosed having at least two chambers containing different ingredients of a medicament separated by an impermeable membrane. A lance is movable independently of a plunger to cut or pierce the membrane before a spring-loaded drive member for the plunger is released to drive a needle out of the body of the injector and discharge the medicament through the needle. A removable safety clip is provided for preventing movement of an actuating cap into an operative position for advancing the lance, and release of the drive member is preventable by a removable safety pin until the injector is to be used. One of the chambers has a needle disposed therein. The sealing structure is conditionable to permit the ingredients to mix in the injector in response to a predetermined actuating procedure before the ingredients are injected.

U.S. Pat. No. 6,474,369 is directed to an apparatus and methods for delivering a lyophilized active medicament with a needle-less injector. A device for storing and mixing an injectate includes a fluid holder removably coupled to an ampoule. The fluid holder initially contains a fluid and the ampoule initially contains a dry reagent. A breakable membrane may be included between the fluid holder and ampoule to prevent the undesirable mixing of the fluid with the dry reagent. Upon application of force to a plunger rod disposed within the fluid holder, fluid is introduced into the ampoule wherein it is mixed with the dry reagent to create an injectable mixture. Air or gas present in the ampoule may be removed therefrom; the fluid holder may be decoupled from the ampoule; and the ampoule may be further coupled to a needle-less injector for administration of an injection of the mixture. The device is particularly useful for lyophilized pharmaceuticals that rapidly lose medicinal efficacy once in solution form.

C. Acid-Neutralizing Solutions

In preferred embodiments, the acid-neutralizing solutions of the present invention may be formed using weak organic or weak inorganic bases, or strong organic or strong inorganic bases or any combinations thereof. The acid-neutralizing solutions of the present invention may also be formed using organic or inorganic buffering agents. In certain embodiments, the acid-neutralizing solutions of the present invention have a pH greater than about 6.5. Preferably, the acid-neutralizing solutions of the present invention have a pH greater than or equal to about 7.0.

Preferably, the acid-neutralizing solutions of the present invention are made using, but are not limited to, calcium carbonate, sodium bicarbonate, sodium carbonate, magnesium oxide, magnesium hydroxide, magnesium trisilicate, magnesium carbonate, aluminum hydroxide, sodium hydroxide, dibasic sodium phosphate, diethanolamine, monobasic sodium phosphate, monoethanolamine, tribasic calcium phosphate or mixtures thereof.

The acid-neutralizing solutions of the present invention may be made using, but are not restricted to, the sodium, potassium, calcium, magnesium and aluminum salts of phosphoric acid, carbonic acid, citric acid or other suitable weak inorganic or organic acids. The acid-neutralizing solutions of the present invention may also be made, but are not restricted to, aluminum, calcium, sodium, potassium and magnesium hydroxides; magnesium oxide; organic pH-buffering substances such as trihydroxymethylaminomethane or other, similar, pharmaceutically acceptable pH-buffering substances.

For purposes of the present invention, neutralization of an acidic solution of *Botulinum* toxin using any of the acid-neutralizing solutions disclosed herein is accomplished by mixing the acid-neutralizing solution with the acidic solution of *Botulinum* toxin such that the pH of the resultant solution after mixing and prior to administration to a patient is about pH 6.5 to about pH 8.0; or about pH 6.6 to about pH 8.0; or about pH 6.7 to about pH 8.0; or about pH 6.8 to about pH 8.0; or about pH 6.9 to about pH 8.0; or about pH 7.0 to about pH 8.0; or about pH 7.0 to about pH 7.9; or about pH 7.0 to about pH 7.8; or about pH 7.0 to about pH 7.7; or about pH 7.0 to about pH 7.6; or about pH 7.0 to about pH 7.5; or preferably about pH 7.0 to about pH 7.4.

In embodiments where two or more solutions are mixed prior to administration, such as, for example, where a solution containing a sequestering agent is combined with an acidic solution of *Botulinum* toxin and an acid-neutralizing solution, the pH of the final solution after mixing and prior to administration to a patient will be about pH 6.5 to about pH 8.0; or about pH 6.6 to about pH 8.0; or about pH 6.7 to about pH 8.0; or about pH 6.8 to about pH 8.0; or about pH 6.9 to about pH 8.0; or about pH 7.0 to about pH 8.0; or about pH 7.0 to about pH 7.9; or about pH 7.0 to about pH 7.8; or about pH 7.0 to about pH 7.7; or about pH 7.0 to about pH 7.6; or about pH 7.0 to about pH 7.5; or preferably about pH 7.0 to about pH 7.4.

In embodiments where a solid form of *Botulinum* toxin (such as a lyophilized or freeze-dried or flash-dried form of *Botulinum* toxin) is mixed with one or more solutions, including an acid-neutralizing solution and, optionally, a solution of one or more sequestering agents, the final pH of the solution after mixing and prior to administration to a patient will be about pH 6.5 to about pH 8.0; or about pH 6.6 to about pH 8.0; or about pH 6.7 to about pH 8.0; or about pH 6.8 to about pH 8.0; or about pH 6.9 to about pH 8.0; or about pH 7.0 to about pH 8.0; or about pH 7.0 to about pH 7.9; or about pH 7.0 to about pH 7.8; or about pH 7.0 to about pH 7.7; or about pH 7.0 to about pH 7.6; or about pH 7.0 to about pH 7.5; or preferably about pH 7.0 to about pH 7.4.

For purposes of the present invention, the amount of an acid-neutralizing solution required to be mixed with an acidic solution of a *Botulinum* toxin may be determined based on the number of equivalents of acid present in the *Botulinum* toxin solution (or the *Botulinum* toxin composition and, optionally the sequestering agent solution) according to well-established chemical principles known to those having skill in the art. As used herein, an equivalent of an acid is the quantity that supplies one mole of $H^+$; an equivalent of a base is the quantity reacting with one mole of $H^+$.

For example, two important characteristics of buffers are buffering capacity and pH. Buffering capacity is the amount of acid or base the buffer can neutralize before the pH begins to change to an appreciable degree. This capacity depends on the amount of acid and base from which the buffer is made. The pH of the buffer depends on the Ka for the acid and on the relative concentrations of the acid and base that comprise the buffer. In general, for a buffer, $pH=pKa+\log([base]/[acid])$. For purposes of this equation, [base] is the concentration of base and [acid] is the concentration of acid. This relationship is known as the Henderson-Hasselbalch equation and is very useful in dealing with buffers. The $pH=pKa$ when the concentration of the acid and its conjugate base are equal. Thus, the pH range of most buffers is limited to the vicinity of the pKa of the acid. For this reason, one usually tries to select a buffer whose acid has a pKa close to the desired pH.

D. *Botulinum* Toxin and Sequestering Agents

Pharmaceutical compositions comprising *Botulinum* neurotoxin and a sequestration agent are described in co-pending U.S. application Ser. No. 10/740,755 filed Dec. 22, 2003 which is hereby incorporated by reference into the present application in its entirety. Use of such pharmaceutical compositions comprising *Botulinum* toxin and a sequestration agent is contemplated in the devices, methods and kits of the present invention, but is not required.

As set forth in the co-pending '755 application, in one embodiment, the sequestration agent is present in the final injectable *Botulinum* toxin formulation in an amount between 550 and 550,000 µg sequestration agent per 100 $LD_{50}$ units *Botulinum* toxin. In another embodiment, the sequestration agent is present in an amount between 550 and 5,500 µg sequestration agent per 100 $LD_{50}$ units *Botulinum* toxin. In a further embodiment, the sequestration agent is present in an amount between 5,500 and 13,000 µg sequestration agent per 100 $LD_{50}$ units *Botulinum* toxin. In a preferred embodiment, the sequestration agent is present in an amount between 13,000 and 50,500 µg sequestration agent per 100 $LD_{50}$ units *Botulinum* toxin. In a more preferred embodiment, the sequestration agent is present in an amount between 50,500 and 505,000 µg sequestration agent per 100 $LD_{50}$ units *Botulinum* toxin. In the most preferred embodiment, the sequestration agent is formulated as encapsulated microspheres in an amount between 50,500 and 90,500 µg sequestration agent per 100 $LD_{50}$ units *Botulinum* toxin.

In another embodiment, the formulations, devices, methods and kits may be practiced with a composition comprising *Botulinum* toxin and a sequestration agent, wherein the sequestration agent is present in an amount between 550 and 900,500 µg sequestration agent per 100 $LD_{50}$ units *Botulinum* toxin. In a further embodiment, the sequestration agent is albumin. In a still further embodiment, the albumin may be formulated as a solid albumin particle.

The *Botulinum* toxin of the present compositions, devices, methods and kits may be selected from a variety of strains of *Clostridium Botulinum*. In a preferred embodiment, the compositions of the present invention comprise a *Botulinum* toxin selected from the group consisting of *Botulinum* toxin types A, B, C, D, E, F and G. In a preferred embodiment, the *Botulinum* toxin is *Botulinum* toxin type A. In a more preferred embodiment, the *Botulinum* toxin is *Botulinum* toxin type A from the Hall strain of *Clostridium Botulinum*.

In another embodiment, the compositions, devices, methods and kits of the present invention comprise a *Botulinum* toxin that consists essentially of fractionated-light-chain *Botulinum* toxin. In yet another embodiment, the *Botulinum* toxin consists essentially of a mixture of hybrid and chain-translocated forms of *Botulinum* toxin. In a further embodiment, the *Botulinum* toxin consists essentially of chimeric forms of *Botulinum* toxin. Although the present invention may utilize any *Botulinum* toxin, *Botulinum* toxin fragment that retains neurotoxic activity, *Botulinum* toxin chimeras and hybrids, chemically-modified *Botulinum* toxin, and specific activities well known to those of ordinary skill in the art, in one embodiment the *Botulinum* toxin is purified to a specific activity greater than or equal to about 20 $LD_{50}$ units per nanogram *Botulinum* toxin.

In certain embodiments, the compositions of *Botulinum* toxin and a sequestration agent are such that the ratio of $LD_{50}$ units of *Botulinum* toxin to µg sequestration agent is less than or equal to about 0.2 for *Botulinum* toxin type A and is less than or equal to about 10 for *Botulinum* toxin type B.

The compositions used in the devices, methods and kits of the present invention, in addition to comprising a *Botulinum* toxin and optionally a sequestration agent, may further comprise a pharmaceutically acceptable carrier and/or zinc and/or a zinc salt. In one embodiment, the *Botulinum* toxin is non-covalently bound to the sequestration agent. In another embodiment, the *Botulinum* toxin is covalently bound to the sequestration agent.

The devices, methods and kits of the present invention may be practiced using compositions of a *Botulinum* toxin and optionally, a sequestration agent, wherein the sequestration agent is selected from the group consisting of: proteins, lipids and carbohydrates. In a preferred embodiment, the sequestration agent is albumin, collagen, epinephrine or hyaluronate. In a more preferred embodiment, the sequestration agent is hyaluronate. In the most preferred embodiment, the sequestration agent is albumin.

The devices, methods and kits of the present invention may also be practiced using compositions comprising a *Botulinum* toxin and, optionally a sequestration agent, wherein the sequestration agent is an albumin, preferably human serum albumin. Furthermore, in one embodiment, the albumin of the present compositions is recombinantly produced. In one embodiment, the albumin is present in an amount between 550 and 5,500 µg albumin per 100 $LD_{50}$ units *Botulinum* toxin. In a further embodiment, albumin is present in an amount between 5,500 and 13,000 µg albumin per 100 $LD_{50}$ units *Botulinum* toxin. In a preferred embodiment, albumin is present in an amount between 13,000 and 50,500 µg albumin per 100 $LD_{50}$ units *Botulinum* toxin. In a more preferred embodiment, albumin is present in an amount between 50,500 and 505,000 µg albumin per 100 $LD_{50}$ units *Botulinum* toxin. In a most preferred embodiment, albumin is formulated as encapsulated microspheres in an amount between 50,500 and 90,500 µg albumin per 100 $LD_{50}$ units *Botulinum* toxin.

In one embodiment of the present invention, the methods of the present invention may be practiced using compositions comprising a *Botulinum* toxin and, optionally, at least one sequestration agent. In a preferred embodiment, the methods of the present invention may be practiced using compositions comprising a *Botulinum* toxin and albumin and further comprising one or more additional sequestration agents.

E. Dosing

Doses used in the systems, devices, methods and kits described herein may range between about 0.6125-25,000 mouse LD 50 units of *Botulinum* toxin per injection depending on the size of the region targeted for injection. Injections may be placed within muscular tissues, integument (skin), joints and perarticular structures, or other tissues. Injections are often made in multiple sites to allow for diffusion of medication and saturation of regional receptors. Multifocal injections may also be employed.

F. Methods of Preparing Pharmaceutical Formulations of *Botulinum* Toxin

It is contemplated that the present invention is directed to methods of using any of the devices or kits described herein for preparing pharmaceutically acceptable formulations of *Botulinum* toxin.

In certain embodiments, the formulation is derived from extracted developed cultures of *Clostridium Botulinum* chemically extracted using acidic solutions and a series of precipitations. Additionally, purification is further accomplished using column chromatography separating contaminating and unnecessary protein contaminants. Purification is monitored using chromatographic gels with known standards. Potency is monitored using LD 50 bioassays conducted with 20-30 gram mice.

G. Kits

It is contemplated that this invention also relates to kits which may be utilized for preparing and administering the formulations of *Botulinum* toxin disclosed herein to a subject in need thereof. It is contemplated that the kits may comprise any of the devices described herein.

In preferred embodiments, the kits comprise the devices disclosed herein comprising a *Botulinum* toxin composition or formulation, one or more acid-neutralizing solutions and, in certain embodiments, one or more solutions of a sequestering agent or agents.

In certain embodiments, the kits may comprise one or more vials, syringes, needles, ampules, cartridges, bottles or other such vessels for storing and subsequently mixing the formulations disclosed herein. In certain embodiments, the devices, vials, syringes, ampules, cartridges, bottles or other such vessels for storing and subsequently mixing the formulations disclosed herein may, or may not have more than one chamber.

In still further embodiments, the acid-neutralizing solution or solutions disclosed herein are stored in one or more graduated vessels (such as a syringe or syringes or other device useful for measuring volumes) so that measured (quantified) amounts of the acid-neutralizing solution may be added or combined with the *Botulinum* toxin composition or formulation and subsequently mixed.

In still further embodiments, the *Botulinum* toxin compositions or formulations disclosed herein are stored in one or more graduated vessels (such as a syringe or syringes or other device useful for measuring volumes) so that measured (quantified) amounts of the *Botulinum* toxin composition(s) or formulation(s) may be added or combined with the acid-neutralizing solution(s) and subsequently mixed.

In still further embodiments, the *Botulinum* toxin compositions or formulations disclosed herein and the acid-neutralizing solutions disclosed herein are stored in one or more graduated vessels (such as a syringe or syringes or other device useful for measuring volumes) so that measured (quantified) amounts of the *Botulinum* toxin formulation and the acid-neutralizing solution may be combined and subsequently mixed.

In certain embodiments, the kits may comprise a *Botulinum* toxin composition or formulation stored within an ampule, vial, syringe, cartridge, bottle or other such vessel and an acid-neutralizing solution stored in a separate ampule, vial, syringe, cartridge, bottle or other such vessel. The ampules, vials, syringes, bottles and other such vessels described herein may or may not be graduated. Prior to administration, the *Botulinum* toxin composition or formulation and the acid-neutralizing solution are combined and mixed. In still further embodiments, the kits may further comprise one or more ampules, vials, syringes, cartridges, bottles or other such vessels for storing one or more solutions of a sequestering agent.

The kits may also comprise one or more anesthetics, preferably local anesthetics. In certain embodiments, the anesthetics are in a ready-to-use formulation, such as, for example an injectable formulation (optionally in one or more pre-loaded syringes) or a formulation that may be applied topically to an area where the *Botulinum* toxin formulations disclosed herein are to be administered. In certain embodiments, the anesthetic is stored dissolved in the acid-neutralizing solution.

Topical formulations of anesthetics may be in the form of an anesthetic applied to a pad, swab, towelette, disposable napkin, cloth, patch, bandage, gauze, cotton ball, Q-TIP™, ointment, cream, gel, paste, liquid, or any other topically applied formulation. Anesthetics for use with the present invention may include, but are not limited to lidocaine, marcaine, cocaine and xylocaine, for example.

The kits may also contain instructions relating to the use of the *Botulinum* toxin compositions or formulations and procedures for mixing, diluting and combining the *Botulinum* toxin compositions or formulations with the acid-neutralizing solution or solutions and, optionally, the sequestering agent or agents. The instructions may also contain detailed descriptions of how to use the devices disclosed herein for mixing and preparing the *Botulinum* toxin formulations prior to administration to a subject in need thereof. The instructions may also contain directions for properly diluting the *Botulinum* toxin formulation or composition with one or more acid-neutralizing solutions and, optionally, one or more sequestering agents, to obtain a desired pH or range of pHs and/or a desired specific activity and/or protein concentration after mixing but prior to administration. The instructions may also contain dosing information. The instructions may also contain material directed to methods for selecting subjects for treatment with the disclosed *Botulinum* toxin formulations. The kits may also include additional buffers, syringes, needles, needle-less injection devices, sterile pads or swabs.

The following Examples serve to illustrate further the present invention and are not to be construed as limiting the scope of the invention in any way.

EXAMPLES

Example 1

Liquid Acidic Preparation of *Botulinum* Toxin and Aqueous Bicarbonate Buffer

A liquid acidic preparation of *Botulinum* toxin is dispensed from a bottle marked storage fluid (low pH). Another bottle is marked diluent (containing an aqueous buffer solution of bicarbonate). The instructions in the package insert will direct the physician to completely mix the solutions, yielding a final concentration of *Botulinum* toxin of 50 U/cc. The physician calculates the dosing to the patients depending on the amount of material to be injected.

Example 2

Kit Comprising Vial of Acidic *Botulinum* Toxin Solution and a Multitude of Vials Containing Acid-Neutralizing Solution A kit comprising a vial of *Botulinum* toxin in a liquid acidic solution and a multitude of vials of one or more acid-neutralizing solutions is delivered to a physician's office. Just prior to administering the *Botulinum* toxin to a patient, the physician removes a measured amount of the acidic *Botulinum* toxin solution using a needle and syringe. The physician injects the measured amount of acidic *Botulinum* toxin formulation into one of the vials of an acid-neutralizing solution and thoroughly mixes the solution to make a pH-neutralized solution of *Botulinum* toxin having a known concentration and/or specific activity of *Botulinum* toxin. Using this solution, the physician proceeds to administer the pH-neutralized solution of *Botulinum* toxin to a patient in need thereof.

Example 3

Kit Comprising Two-Chambered Vial or Ampule with Breakable Seal Containing Acidic *Botulinum* Toxin Formulation and Acid-Neutralizing Solution A kit comprising a two-chambered vial or ampule in which one of the chambers contains *Botulinum* toxin in a liquid acidic solution and the second chamber contains an acid-neutralizing solution is delivered to a physician's office. Just prior to administering the *Botulinum* toxin to a patient, the physician breaks the seal separating the two chambers of the vial or ampule and allows the solutions to mix. The resultant pH-neutralized solution of *Botulinum* toxin has a known protein concentration and/or specific activity of *Botulinum* toxin. Using this solution, the physician proceeds to administer the pH-neutralized solution of *Botulinum* toxin to a patient in need thereof.

Example 4

Syringe with Breakable Seal Containing Acidic Solution of *Botulinum* Toxin and an Acid Neutralizing Solution A disposable syringe containing two chambers separated by a breakable seal is loaded with an acidic solution of *Botulinum* toxin and an acid-neutralizing solution, such as a bicarbonate solution. The pre-loaded syringe may be stored at room temperature or in a refrigerator at approximately 4° C. until use. Just prior to administration to a patient in need thereof, the seal separating the two chambers within the syringe is broken, allowing the acidic solution of *Botulinum* toxin and the acid-neutralizing solution to mix. The injection solution is thoroughly mixed and administered to a patient in need thereof.

It will be readily seen by one of ordinary skill in the art that the present invention fulfills all of the objects set forth above. After reading the foregoing specification, one of ordinary skill will be able to effect various changes, substitutions of equivalents, and various other aspects of the invention as broadly disclosed herein. It is therefore intended that the protection granted herein be limited only by the definition contained in the appended claims and equivalents thereof.

The invention claimed is:

1. A device comprising at least two chambers, wherein a first chamber comprises an acidic solution of *Botulinum* toxin, and a second chamber comprises an acid-neutralizing solution, wherein the acid-neutralizing solution is present in an amount sufficient to raise the pH of the acidic *botulinum* toxin solution to from about pH 7.0 to about pH 7.5 after mixing.

2. The device of claim 1, wherein said device comprises at least three chambers.

3. The device of claim 2, wherein a third chamber comprises a solution comprising one or more sequestering agents.

4. The device of claim 1, wherein said chambers comprise one or more barriers or seals separating the chambers.

5. The device of claim 4, wherein said one or more barriers or seals may be broken or breached or ruptured or punctured or rendered ineffective in preventing mixing of said solutions, to allow the contents of each chamber to mix.

6. The device of claim 1, wherein the pH of said acidic solution of *Botulinum* toxin is about 1.0 to about 6.9.

7. The device of claim 6, wherein the pH of said acidic solution of *Botulinum* toxin is about 2.0 to about 6.9.

8. The device of claim 7, wherein the pH of said acidic solution of *Botulinum* toxin is about 2.5 to about 6.8.

9. The device of claim 8, wherein the pH of said acidic solution of *Botulinum* toxin is about 2.5 to about 6.7.

10. The device of claim 1, wherein said acidic solution of *Botulinum* toxin comprises any combination of one or all of immunotypes A-G.

11. The device of claim 1, wherein said acidic solution of *Botulinum* toxin comprises about 1 to about 2000 LD 50 units of *Botulinum* toxin.

12. The device of claim 1, wherein said acid-neutralizing solution comprises one or more bases selected from the group consisting of weak bases, strong bases, inorganic bases, and organic bases.

13. The device of claim 1, wherein said acid-neutralizing solution comprises a buffering agent.

14. The device of claim 13, wherein said buffering agent is an organic buffer or an inorganic buffer or any combination of organic and inorganic buffers.

15. The device of claim 1, wherein said acid-neutralizing solution is present in an amount sufficient to raise the pH of said *Botulinum* toxin solution to from about pH 7.0 to about pH 7.4 after mixing.

16. The device of claim 1, wherein said acid-neutralizing solution is selected from the group consisting of a bicarbonate solution, a phosphate solution, a carbonate solution, a sodium hydroxide solution, a potassium hydroxide solution, a calcium hydroxide solution, an aluminum hydroxide solution, and any combination of these solutions.

17. A method of preparing a pharmaceutical formulation of *Botulinum* toxin comprising combining an acidic solution of *Botulinum* toxin and an acid-neutralizing solution in a device of claim 1, wherein the pH of said *botulinum* toxin formulation after mixing is from about pH 7.0 to about pH 7.5.

18. A method of claim 17, further comprising mixing a measured volume of said acid-neutralizing solution with said acidic formulation of *Botulinum* toxin, wherein the pH of said *botulinum* toxin formulation after mixing is from about pH 7.0 to about pH 7.5.

19. A method of preparing a pharmaceutical formulation of *Botulinum* toxin comprising withdrawing a measured volume of an acid-neutralizing solution from the device of claim 1 and mixing said measured volume with said acidic *Botulinum* toxin formulation in the device of claim 1, wherein the pH of said *botulinum* toxin formulation after mixing is from about pH 7.0 to about pH 7.5.

20. A kit comprising a device for preparing a pharmaceutical formulation of *Botulinum* toxin, wherein said kit comprises the device of claim 1.

21. A kit of claim 20, wherein said kit further comprises a solution of a sequestering agent.

* * * * *